United States Patent [19]

Wakabayashi et al.

[11] Patent Number: 5,344,973
[45] Date of Patent: Sep. 6, 1994

[54] PROCESS FOR PREPARATION OF LITHIUM N-METHYLAMINO BUTYRATE

[75] Inventors: Makoto Wakabayashi; Minoru Senga; Yoshinari Koyama, all of Chiba, Japan

[73] Assignee: Idemitsu Petrochemical Company Limited, Tokyo, Japan

[21] Appl. No.: 87,262

[22] Filed: Jul. 8, 1993

[30] Foreign Application Priority Data

Jul. 10, 1992 [JP]  Japan .................................. 4-183717

[51] Int. Cl.$^5$ ............................................. C07C 205/00
[52] U.S. Cl. ...................................................... 562/553
[58] Field of Search ........................................ 562/553

[56] References Cited

U.S. PATENT DOCUMENTS 3,867,356  2/1975  Campbell ............................. 562/553
4,324,886  4/1982  Edmonds ............................. 562/553
4,371,706  1/1983  Edmonds ............................. 562/553
4,529,818  7/1985  Nesheiwat .......................... 562/553

Primary Examiner—Michael L. Shippen
Attorney, Agent, or Firm—Nikaido, Marmelstein, Murray & Oram

[57] ABSTRACT

A novel process for preparing lithium N-methylaminobutyrate, which is useful for preparation of poly(arylene sulfide) such as poly(phenylene sulfide). The process comprises reacting N-methyl-2-pyrrolidone with a hydroxide of an alkali metal other than lithium in an aprotic organic solvent, reacting the resulting reaction product mixture with lithium chloride after removing water therefrom and removing the alkali metal chloride formed as a by-product. According to this process, lithium N-methylaminobutyrate lithium free from alkali metal other than lithium, is easily prepared, which is easily recovered and recycled in the production of said polymers.

12 Claims, 1 Drawing Sheet

PROCESS FOR PREPARATION OF LITHIUM N-METHYLAMINO BUTYRATE

Field of the Invention

The present invention relates to a process for preparation of lithium N-methylaminobutyrate. More particularly, the invention relates to a process for preparation of lithium N-methylaminobutyrate, which can be especially suitably used in the production of polyarylene sulfide (hereinafter, occasionally referred to as "PAS") resins such as polyphenylene sulfide (hereinafter, occasionally referred to as "PPS") resins.

BACKGROUND OF INVENTION

Polyarylene sulfide (PAS) resins, especially polyphenylene sulfide (PPS) resins, are well known as engineering resins having high rigidity, excellent mechanical strength, heat-resistance, etc. and useful as materials for various electronic and electric appliances and others for which high rigidity is required. These resins are conventionally prepared by reacting a dihaloaromatic compound such as p-dichlorobenzene with a sodium-sulfur compound such as sodium hydrosulfide in an aprotic organic solvent such as N-methyl-2-pyrrolidone (hereinafter occasionally referred to as NMP). In this process, however, the formed sodium chloride is insoluble in the reaction solvent such as NMP and, therefore, it is inevitably incorporated in the produced resin, which can hardly be removed by washing.

When lithium compound is used instead of sodium compound, the lithium chloride formed as a by-product is soluble in many aprotic organic solvents including NMP and, therefore, the lithium content in the produced resin is easily reduced. Thus employment of a lithium compound is now spotlighted.

In U.S. Pat. No. 4,451,343 it is disclosed that PAS resins including PPS resin can be produced batch-wise or continuously by the reaction of lithium N-methylaminobutyrate (hereinafter occasionally referred to as LMAB), which is formed by the reaction of lithium hydroxide and NMP, a dihaloaromatic compound such as p-dichlorobenzene and hydrogen sulfide. This process is advantageous in that the amount of an alkali metal taken into the produced polymer is far smaller in comparison with the process in which solvent-insoluble sodium chloride is formed, since the polymer such as the PPS resin is produced by using LMAB, which is a lithium compound, as a starting material instead of sodium compound and thus solvent-soluble lithium chloride is formed.

However, lithium is far more costly in comparison with sodium. Therefore, in order to save the production cost, it is imperative that the by-product lithium compound is recovered and reused.

In the above-outlined known process, the LMAB (lithium N-methylaminobutyrate) is used in the form of a reaction mixture obtained by the reaction of lithium hydroxide ($LiOH \cdot H_2O$) and NMP.

Lithium hydroxide is sparingly soluble in NMP and, therefore, the mixture is a slurry, which is not convenient in transportation, agitation, etc. in comparison with a solution.

Also, in said process, lithium hydroxide is used as a starting material and lithium chloride is formed in the production of the polymer. When the formed lithium chloride is recovered and reused, it must be converted to lithium hydroxide by any means. It is described in said U.S. patent specification that the lithium chloride aqueous solution recovered from the reaction mixture after the preparation of the polymer and the produced lithium chloride is converted to lithium hydroxide by the reaction with sodium hydrogen carbonate or by means of electrolysis.

However, conversion of lithium chloride to lithium hydroxide for reuse, including the above-mentioned processes, is not desirable from the viewpoint of production cost.

That is, the procedure to form lithium N-methylaminobutyrate from lithium hydroxide and N-methyl-2-pyrrolidone is not satisfactory as a method for preparing high purity lithium N-methylaminobutyrate and as a step of a process for preparation of PAS resins including PPS resins, since the purity of the lithium N-methylaminobutyrate is low (91.5% or so) and thus removal of insoluble impurity lithium compounds from the produced polymer by washing is difficult and it is very disadvantageous to convert the recovered lithium chloride to lithium hydroxide.

Therefore, it would be most desirable to develop a process for preparing high purity N-methylaminobutyrate from N-methyl-2-pyrrolidone and further to prepare PAS resins including PPS resins by forming the starting material lithium N-methylaminobutyrate not from lithium hydroxide but from lithium chloride, which is recovered from the polymer product mixture.

Under the circumstances, in order to solve the above problems, we conducted an intensive study in search of a process to efficiently prepare high purity lithium N-methylaminobutyrate, which can be advantageously used as a starting material for production of PAS resins including PPS resins, from N-methyl-2-pyrrolidone and lithium chloride.

The present invention was made under the above-described circumstances.

The object of the invention is to provide a process for efficiently preparing high purity lithium N-methylaminobutyrate from N-methyl-2-pyrrolidone using lithium chloride instead of lithium hydroxide, and thus enabling easy recycling of the by-product lithium chloride and purification of the polymer product, which were problems in the known process for production of PAS resins including PPS resins by the reaction of lithium N-methylaminobutyrate, a dihaloaromatic compound and hydrogen sulfide.

Thus we have found that high quality N-methylaminobutyrate-pyrrolidone, which satisfies to achieve the above mentioned object, can be prepared by reacting N-methyl-2-pyrrolidone with an alkali metal hydroxide other than lithium hydroxide in a suitable solvent (usually aqueous solution) to form an alkali metal (other than lithium) salt of N-methylaminobutyrate, removing water from the reaction product mixture and adding lithium chloride thereto to convert the alkali salt to the lithium N-methylaminobutyrate, separating the formed by-product alkali metal (other than lithium) chloride by deposition, etc.

SUMMARY OF THE INVENTION

The present invention provides a process for preparing N-methylaminobutyrate comprising reacting N-methyl-2-pyrrolidone with hydroxide of an alkali metal other than lithium, removing water from the reaction product mixture, adding lithium chloride to the mixture and removing the formed alkali metal chloride.

In the process of the present invention, the removal of water should be preferably carried out until the water content becomes not more than 500 wtppm.

In the process of the present invention, a preferred aprotic organic solvent is N-methyl-2-pyrrolidone.

In the process of the present invention, a preferred alkali metal hydroxide to be reacted with N-methyl-2-pyrrolidone is sodium hydroxide.

In the process of the present invention, it is preferred to remove the sodium chloride formed as a by-product from the reaction product mixture containing lithium N-methylaminobutyrate and said sodium chloride by depositing at a temperature of 80°–200° C.

DISCLOSURE OF THE INVENTION

In the process of the present invention, an alkali metal (other than lithium) salt of N-methylaminobutyric acid is prepared by reacting N-methyl-2-pyrrolidone with hydroxide of an alkali metal other than lithium in an aprotic organic solvent.

Hereinafter, the alkali metal (other than lithium) salt of N-methylaminobutyric acid is referred to as "AMAB" in order to distinguish it from lithium N-methylaminobutyrate (LMAB). In the process of the present invention, the step of preparing AMAB is referred to as "AMAB synthesis step". Of the AMAB synthesis step, the step in which sodium N-methylaminobutyrate is prepared is referred to as "sodium N-methylaminobutyrate synthesis step".

In the AMAB synthesis step, N-methyl-2-pyrrolidone is used a starting material. The N-methyl-2-pyrrolidone need not necessarily be of high purity but those of technical grade or solvent grade can be used and not only commercially available products but also house-synthesized products, recovered products, etc. of lower purity or grade can be used. The N-methyl-2-pyrrolidone also can be suitably used as an aprotic organic solvent alone or mixed with other solvents.

As mentioned above, in the AMAB synthesis step an aprotic organic solvent is used. General aprotic polar compounds such as amides, lactams, urea compounds, organic sulfur compounds, cyclic organic phosphorus compounds, etc. can be suitably used.

Of these aprotic polar organic compounds, examples of amide compounds N,N-dimethylformamide, N,N-diethylformamide, N,N-dimethylacetamide, N,N-diethylacetamide, N,N-dipropylacetamide, N,N-dimethylbenzoic acid amide, etc.

Examples of lactam compounds are caprolactam; N-alkylcaprolactams such as N-methylcaprolactam, N-ethylcaprolactam, N-isopropylcaprolactam, N-isobutylcaprolactam, N-n-propylcaprolactam, N-n-butylcaprolactam, N-cyclohexylcaprolactam, N-methyl-2-pyrrolidone, N-ethyl-2-pyrrolidone, N-isopropyl-2-pyrrolidone, N-isobutyl-2-pyrrolidone, N-n-propyl-2-pyrrolidone, N-n-butyl-2-pyrrolidone, N-cyclohexyl-2-pyrrolidone, N-methyl-3-methyl-2-pyrrolidone, N-ethyl-3-methyl-2-pyrrolidone, N-methyl-3,4,5-trimethyl-2-pyrrolidone, N-methyl-2-piperidone, N-ethyl-2-piperidone, N-isopropyl-2-piperidone, N-methyl-6-methyl-2-piperidone, N-methyl-3-ethyl-2-piperidone, etc.

Examples of said urea compounds are tetramethylurea, N,N'-dimethylethyleneurea, N,N'-dimethylpropyleneurea, etc.

Examples of said sulfur compounds are dimethylsulfoxide, diethylsulfoxide, diphenylsulfone, 1-methyl-1-oxosulforane, 1-ethyl-1-oxosulforane, 1-phenyl-1-oxosulforane, etc. Examples of said cyclic organic phosphorus compounds are 1-methyl-1-oxophosphorane, 1-n-propyl-1-oxophosphorane, 1-phenyl-1-oxophosphorane, etc.

These aprotic organic compound solvents can be used alone or as a mixture of two or more. Or they can be used as a mixture with other solvents which are harmless in the process of the present invention as an aprotic organic solvent.

Of these aprotic organic solvents, the most preferable are an N-alkylcaprolactam and an N-alkyl-2-pyrrolidone. N-methyl-2-pyrrolidone is especially preferred. As N-methyl-2-pyrrolidone is a starting material for reaction with hydroxide of alkali metal other than lithium, employment thereof as a solvent allows the reaction very advantageously and is very preferable from the viewpoint of the process of the present invention as a whole. Further N-methyl-2-pyrrolidone is preferable as a solvent in the production of said PAS resins including PPS resins. Thus this is an especially desirable solvent in the process of the present invention.

It is usually preferred in the reaction in the AMAB synthesis step to supply a non-lithium alkali metal hydroxide as an aqueous solution. Thus the reaction is conducted in a mixed solvent system of said aprotic organic solvent and water.

In said AMAB synthesis step, hydroxide of an alkali metal other than lithium is used as the reactant to be reacted with said N-methyl-2-pyrrolidone. Hereinafter the hydroxide of an alkali metal other than may be said as non-lithium alkali metal hydroxide. Non-lithium alkali metal hydroxides are sodium hydroxide, potassium hydroxide, rubidium hydroxide, cesium hydroxide or a mixture of two or more thereof. Of these, sodium hydroxide and potassium hydroxide are preferable and sodium hydroxide is most preferable. The non-lithium hydroxides such as sodium hydroxide need not be pure but those of ordinary technical grade can be conveniently used.

The non-lithium alkali metal hydroxide is usually supplied to the reaction system in the form of an aqueous solution.

The preferred conditions of the reaction in the AMAB synthesis step are as follows. They are explained with respect to synthesis of sodium N-methylaminobutyrate, since synthesis of sodium N-methylaminobutyrate using sodium hydroxide as a non-lithium alkali metal hydroxide is most preferred. When non-lithium alkali metal hydroxides other than sodium hydroxide are used, the reaction can be carried out in the same manner by molar conversion of the amounts used.

Sodium N-methylaminobutyrate can be suitably prepared under the following conditions.

Sodium N-methylaminobutyrate can be prepared from sodium hydroxide and N-methyl-2-pyrrolidone.

As described above, the reaction can be carried out in various aprotic organic solvents but it is desirable to use N-methyl-2-pyrrolidone as a solvent. In this case, N-methyl-2-pyrrolidone is a reactant and simultaneously an aprotic organic solvent.

When N-methyl-2-pyrrolidone is used as an aprotic organic solvent in the preparation of sodium N-methylaminobutyrate, the ratio of N-methyl-2-pyrrolidone, which is used as a reactant as well as a solvent, to sodium hydroxide is 1.05–30 mol, preferably 1.20–5.0 mol. When a solvent other than N-methyl-2-pyrrolidone is used as a aprotic solvent, which may be mixed with N-methyl-2-pyrrolidone, the N-methyl-2-pyrrolidone as the reactant should be used in an amount of not less than 1.05 mol per mol sodium hydroxide. In this case, it is preferable that the total amount of the N-methyl-2-pyrrolidone and the aprotic solvent should preferably be 1.05–30 mol, preferably 1.20–5.0 mol per mol sodium hydroxide.

Incidentally, when an aprotic organic solvent other than N-methyl-2-pyrrolidone is used, 1.5–30 mol, preferably 1.2–10 mol N-methyl-2-pyrrolidone per mol of non-lithium alkali metal hydroxide is used.

Sodium hydroxide as a starting material is preferably used in the form of an aqueous solution, the concentration of which is usually 5–90 wt %, preferably 40–50 wt %. By using sodium hydroxide solution of such a concentration, the reaction system can be kept more homogeneously and the reaction can be efficiently conducted. The hydroxide of non-lithium alkali metal other than sodium can be used in the same manner as in the case of sodium hydroxide.

Usually the reactions can be suitably carried out at a reaction temperature of 100°–200° C. The reaction time is usually 0.1–10 hours or so although it varies depending upon reaction temperature and other reaction conditions.

As described above, sodium N-methylaminobutyrate can be suitably synthesized, wherein it is preferred that the sodium hydroxide is converted to sodium N-methylaminobutyrate as completely as possible.

The above described synthesis of sodium N-methylaminobutyrate can be easily translated to the general AMAB synthesis step. That is, N-methylaminobutyrate of non-lithium alkali metals other than sodium can be synthesized in accordance with the above described procedures.

In the process of the present invention, from the AMAB such as sodium N-methylaminobutyrate obtained in the AMAB synthesis step, water is removed so as to reduce the water content thereof.

This removal of water can be effected by ordinary means such as distillation. In this case, it is no problem if a portion of the solvent is removed simultaneously.

Although the thus synthesized AMAB such as sodium N-methylaminobutyrate can be isolated at this stage, usually, the reaction product mixture from which water has been removed, can advantageously be transferred to the next process step (the lithium N-methylaminobutyrate synthesis step) as is or after suitably modifying the amount of the solvent as desired.

Removal of water should preferably be effected so that the water content in the reaction product mixture after water removal, which is to be supplied to the lithium N-methylaminobutyrate synthesis, is preferably not more than 500 wtppm. If the mixture, in which the water content is more than 500 wtppm, is sent to the lithium N-methylaminobutyrate synthesis step, the formed alkali metal chloride such as sodium chloride tends to be eluted as $Na^+$ ion, etc. together with water into the lithium N-aminobutyrate solution, that is, the sufficient removal of the formed alkali metal chloride is difficult.

In the process of the present invention, the thus obtained dehydrated solution of the AMAB such as sodium N-methylaminobutyrate is reacted with lithium chloride so as to give lithium N-methylaminobutyrate. Here, chloride of the alkali metal formed as a by-product by reaction of AMAB such as sodium N-methylaminobutyrate and lithium chloride is removed as completely as possible so that the desired solution containing lithium N-methylaminobutyrate is obtained. The step in which lithium N-methylaminobutyrate is prepared is referred to as "lithium N-methylaminobutyrate synthesis step" and the step in which the formed alkali metal chloride such as sodium chloride is removed is referred to as "alkali metal chloride removal step".

In the lithium N-methylaminobutyrate synthesis step, lithium chloride is used. Although fresh lithium chloride is a commercially available material, the object of the present invention is more effectively achieved by using the lithium chloride which is recovered and recycled from the process of preparing PAS resins such as PPS resins using lithium N-methylaminobutyrate, inter alia the N-methylaminobutyrate prepared by the process of the present invention.

Although the lithium chloride can be supplied to the reaction system in the form of powder or slurry, it is preferred to use it as a solution in one of said aprotic organic solvents, especially N-methyl-2-pyrrolidone. Use of N-methyl-2-pyrrolidone is especially desirable throughout the steps, since N-methyl-2pyrrolidone exhibits a high solubility to lithium chloride, can be advantageously used in the sodium N-methylaminobutyrate (AMAB) synthesis step and further it is also a good polymerization medium in the preparation of PAS resins such as PPS resins.

The preferable conditions employed in the lithium N-methylaminobutyrate step are as follows. In the process of the present invention, it is most suitably employed to supply the solution containing sodium N-methylaminobutyrate obtained by the sodium N-methylaminobutyrate synthesis step and the water removal step into the lithium N-methylaminobutyrate synthesis step. Therefore, the step on which sodium N-methylaminobutyrate is used for preparation of lithium N-methylaminobutyrate is specifically described. The conditions can be easily translated into the ease of an AMAB synthesis step by molar conversion of time amounts of used materials.

In the process of the present invention, the synthesis of lithium N-methylaminobutyrate can be suitably carried out under the following condition by using the above-described solution containing sodium N-methylaminobutyrate from which water has been removed and solution containing said lithium chloride, which may be N-methyl-2-pyrrolidone solution and recovered solution obtained in the step of preparation of PAS resin such as PPS resin.

The sodium N-methylaminobutyrate solution is preferably a solution having N-methyl-2-pyrrolidone as solvent and usually the concentration thereof should preferably be 5–95 wt %, As described above, the water content of the solution should preferably be not more than 500 wt ppm.

Usually the proportion of the sodium N-methylaminobutyrate and lithium chloride to be used is preferably 1–5 mol, more preferably 1–1.50 mol lithium chloride per mol sodium N-methylaminobutyrate.

Usually the reaction for producing lithium N-methylaminobutyrate is preferably carried out at a temperature of 100°–200° C. The suitable reaction time is usually 0.1–10 hours although it varies depending upon reaction temperature and other conditions.

Thus lithium N-methylaminobutyrate can be suitably prepared from sodium N-methylaminobutyrate as described above, sodium N-methylaminobutyrate should preferably be converted to lithium N-methylaminobutyrate as completely as possible.

Needless to say, the above-described lithium N-methylaminobutyrate synthesis step using sodium N-methylaminobutyrate can be translated into the lithium N-methylaminobutyrate synthesis using another AMAB.

In the process of the present invention, the formed alkali metal chloride is removed from the reaction product mixture obtained from the lithium N-methylaminobutyrate synthesis step and containing lithium N-methylaminobutyrate and an alkali metal chloride as by product. In the above described lithium N-methylaminobutyrate synthesis step in which sodium N-methylaminobutyrate is used, sodium chloride is formed and this is removed as a by-product.

The removal of alkali metal chloride such as sodium chloride can suitably be performed by depositing the chloride crystals and separating them by usual solid-liquid separation means such as filtration. Usually deposition of alkali metal chloride such as sodium chloride is preferably carried out at a temperature of 80°-200° C. At a temperature lower than 80° C., the solubility of lithium N-methylaminobutyrate is small and separation cannot efficiently be effected. On the other hand, at a temperature higher than 200° C., there may be problems such as decomposition of lithium N-methylaminobutyrate, etc.

It may well be conducted to concentrate the solution to suitably reduce the amount of the solvent prior to deposition.

Thus, a high purity lithium N-methylaminobutyrate solution (usually in N-methyl-2-pyrrolidone), in which the content of alkali metal other than lithium is extremely low, can be easily obtained. In fact, the concentration of sodium ions (generally speaking, ions of an alkali metal other than lithium) can be made about 1000 ppm or less.

From the thus obtained lithium N-methylaminobutyrate solution, high purity lithium N-methylaminobutyrate can be collected in the form of crystals or the like by removing the solvent and further removing the residual lithium chloride as desired. However, the lithium N-methylaminobutyrate solution can be used as a starting material for preparation of PAS (such as PPS) resins as is or by modifying the concentration thereof as desired.

The lithium N-methylaminobutyrate solution in accordance with the process of the present invention contains extremely low concentration of alkali metals other than lithium such as sodium, and, therefore, the polymers prepared therefrom also contain only extremely small amounts of alkali metals other than lithium. Even if the lithium N-methylaminobutyrate solution contains a small amount of the residual unreacted lithium chloride, it has a sufficient solubility in N-methyl-2-pyrrolidone or the like, which is usually used as a solvent for polymerization and washing of the produced polymer, and the lithium N-methylaminobutyrate solution obtained in the process of the present invention does not contain other lithium compounds, which are sparingly soluble or insoluble in N-methyl-2-pyrrolidone or the like. Therefore, incorporation of other lithium components hardly soluble in N-methyl-2-pyrrolidone is greatly reduced. Thus the lithium content in the formed polymer is remarkably reduced since the residual lithium components can be satisfactorily removed by washing with a small amount of N-methyl-2-pyrrolidone or the like without using a large amount of water or warm water as in the case of the conventional process.

The preparation of PAS resins including PPS resins using the lithium N-methylaminobutyrate obtained by the process of the present invention can be carried out in the same manner as the conventional processes. The lithium chloride or a solution thereof produced as a by-product in the polymerization can be recycled to the above described lithium N-methylaminobutyrate synthesis step as a starting material or a solution thereof. The N-methyl-2-pyrrolidone, which is recovered in the stage of the polymer production, can be suitably used as a starting material or a solvent in the process of the present invention.

The preparation of lithium N-methylaminobutyrate in accordance with the present invention can be carried out by a batch process, in which each step is conducted independently, or a continuous process, in which the steps are continuously connected, or otherwise, by a combination of batch process and continuous process. However, usually a continuous process is suitably employed.

Now the invention will be specifically described with reference to the attached drawing.

BRIEF DESCRIPTION OF THE DRAWINGS

The attached

SPECIFIC DESCRIPTION OF THE INVENTION

Figure 1:
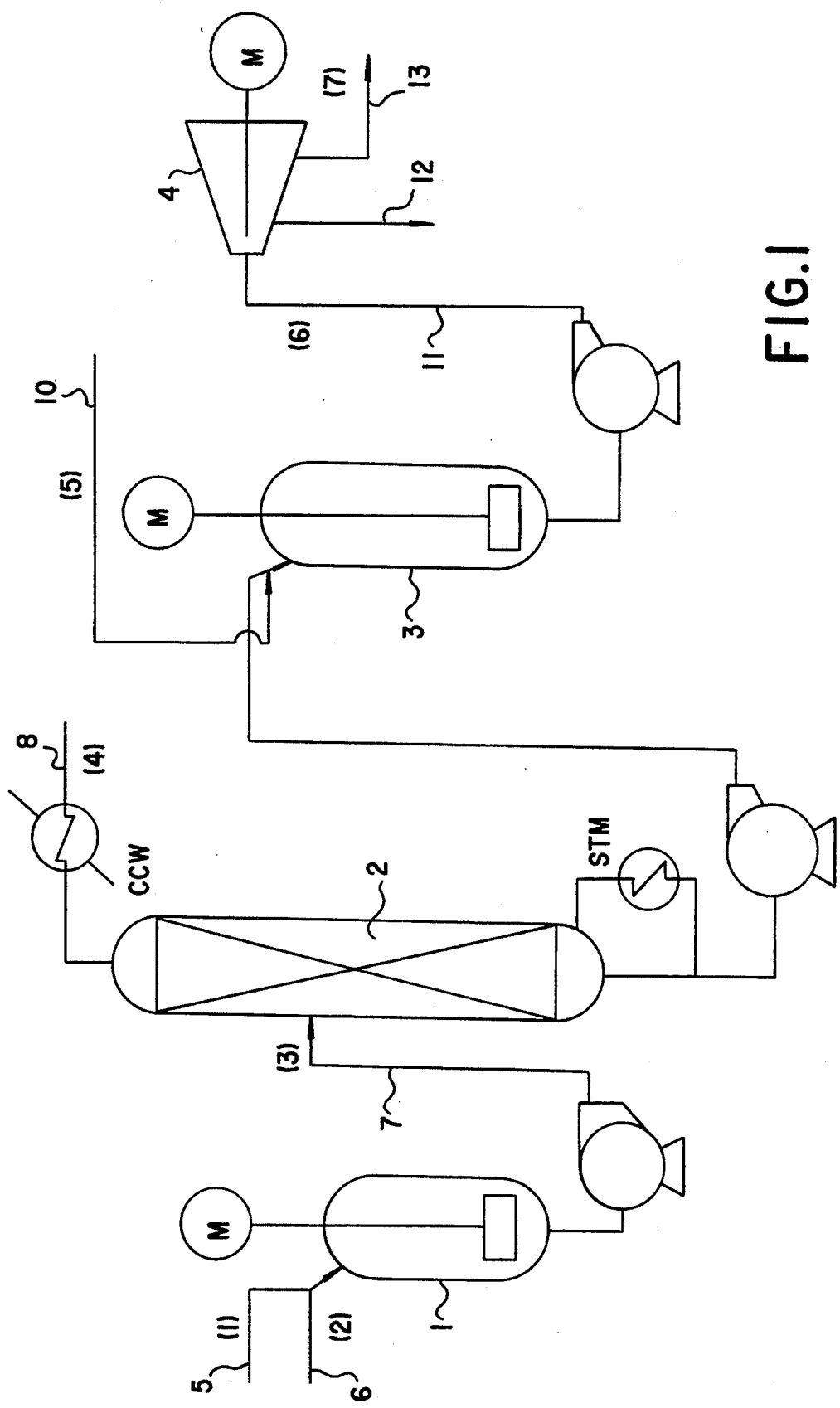
FIG. 1 is a generalized flow diagram of a preferable continuous process in accordance with the present invention representing a continuous production system.

An example of process steps of a preferred continuous process is illustrated in FIG. 1 as a flow diagram.

FIG. 1 shows a preferred example of the continuous process (a production line) for obtaining lithium N-methylaminobutyrate solution comprising a sodium N-methylaminobutyrate synthesis step using sodium hydroxide, a water removal step, a lithium N-methylaminobutyrate synthesis step and a sodium chloride removing step.

In the example represented by FIG. 1, a sodium hydroxide solution as starting material 5 and N-methyl-2-pyrrolidone 6 as both of starting material and solvent are supplied into a sodium N-methylaminobutyrate synthesis tank 1, wherein sodium N-methylaminobutyrate is synthesized. The obtained reaction product mixture solution 7, namely, the sodium N-methylaminobutyrate-solution is continuously sent to a distillation tower 2, wherein a desired amount of water is removed and the removed water 8 is taken out of the reaction system from the tower top. Incidentally, N stands for a motor, CCW stands for circulation cooling water, and STM stands for steam.

The dewatered reaction mixture 9, i.e., the sodium N-methylaminobutyrate solution, whose water content is reduced to not more than 500 wtppm, is sent to a lithium N-methylaminobutyrate synthesis tank 3. An N-methyl-2-pyrrolidone solution of lithium chloride 10 as a starting material for preparation of lithium N-methylaminobutyrate is supplied to the lithium N-methylaminobutyrate synthesis tank 3, wherein the lithium N-methylaminobutyrate synthesis is effected. The obtained reaction product mixture 11, i.e., a solution containing the formed lithium N-methylaminobutyrate and sodium chloride, is transferred to a decantor 4, wherein the sodium chloride 12 is separated as solid by deposition and taken out of the reaction system.

The lithium N-methylaminobutyrate solution from which sodium chloride has been removed 13, i.e., the N-methyl-2-pyrrolidone solution of the formed lithium N-methylaminobutyrate is recovered from the decantor 4. The recovered lithium N-methylaminobutyrate solution 13 can be suitably used as a starting material for production of PAS resins such as PPS resins as is, and can be continuously supplied to the polymerization step.

Examples of typical operation conditions, materials of apparatuses, etc. in the process (continuous production equipment) corresponding to FIG. 1 are indicated in Table 1.

TABLE 1

| Apparatus | Operation Conditions | | Material |
|---|---|---|---|
| | Temp. °C. | Resid. time (hr) | |
| SMAB synth. tank | 160 | 0.5 | SUS316L |
| Distil. tower | 210 | | SUS316L |
| LMAB synth. tank | 150 | 0.5 | SUS304 |
| Decantor | 150 | | SUS316 |

Now the invention is illustrated by way of working examples and comparative examples. Needless to say, the invention is never to be restricted to these working examples.

EXAMPLE 1

In a 10 liter autoclave equipped with an agitating propeller, an aqueous solution comprising 4,460 g (45.0 mol) of N-methyl-2-pyrrolidone, 400 g (10.0 mol) of sodium hydroxide and 417 g of water was placed. The reaction was conducted at 160° C. under 300 rpm rotation for 1 hour. Then 500 ml of N-methyl-2-pyrrolidone containing water was taken out of the reaction system. After cooling, 445 g (10.5 mol) of lithium chloride and N-methyl-2-pyrrolidone were added to the reaction system and the mixture was allowed to react at 150° C. under 300 rpm rotation for 1 hour. The content was poured onto a sintered glass filter (G4) kept at 100° C. and subjected to suction filtration. When the filtrate was cooled to room temperature, white crystals deposited. The white crystals were washed twice with acetone and dried. The white crystalline substance was identified as lithium N-methylaminobutyrate by chemical analysis of lithium ions, FT-IR and NMR analysis. The yield was 90%. The purity was measured by ion chromatography and the conversion was proved to be 99.8%.

EXAMPLES 2–6

Lithium N-methylaminobutyrate was synthesized under the conditions indicated in Table 2 by the procedures of Example 1. The results are also shown in Table 2 together with the conditions and results of Example 1.

TABLE 2

| Ex. | NaOH conc. (wt %) | SMAB conc, (wt %) | LMAB conc, (wt %) | Yield (%) | Purity (%) |
|---|---|---|---|---|---|
| 1. | 49 | 29 | 26 | 90 | 99.8 |
| 2. | 49 | 36 | 23 | 87 | 98.8 |
| 3. | 49 | 36 | 26 | 86 | 99.1 |
| 4. | 49 | 51 | 30 | 89 | 98.8 |
| 5. | 49 | 58 | 33 | 86 | 99.3 |
| 6. | 49 | 80 | 41 | 88 | 99.0 |

Comparative Example

In the 10 liter autoclave used in Example 1, 420 g (10.0 mol) of lithium hydroxide monohydrate, 3,000 ml of N-methyl-2-pyrrolidone and 4,000 ml of water were placed and the mixture was allowed to react at 100° C. under the rotation of 300 rpm for 3 hours. The reaction product was distilled over a period of 4 hours. The temperature of the dehydrated product was 130° C. The collected product was washed with acetone twice and dried. The yield and purity were measured and the results were as follows. Yield: 85%. Purity: 91.5%.

EXAMPLES 7–9

The process of the present invention was repeated using an apparatus represented by FIG. 1 under the operation conditions indicated in Table 3. The results are shown in Table 4. The conditions of separation in the distillation tower 2 were as follows. The water content of the bottom was 200 wtppm and the N-methyl-2-pyrrolidone content was 50 wtppm.

TABLE 3

| Ex. | NMP feed (l/min) | 48% NaOH feed (l/min) | React. temp. in tank 1 (°C.) | Res. time in tank 1 (hr) | SMAB feed (l/min) | Dehyd'n (l/min) | LiCl feed (l/min) |
|---|---|---|---|---|---|---|---|
| 7 | 2 | 0.3 | 160 | 0.5 | 2.2 | 0.20 | 0.86 |
| 8 | 1 | 0.3 | 160 | 0.5 | 1.3 | 0.20 | 0.86 |
| 9 | 0.5 | 0.3 | 160 | 0.5 | 0.8 | 0.20 | 0.86 |

TABLE 4

| Ex. | React. Temp. Tank 3 (°C.) | Res. Time Tank 3 (hr) | SMAB feed (l/min) | Treatment Temp. (°C.) | LMAB feed (l/min) | LMAB pur'ty (%) |
|---|---|---|---|---|---|---|
| 7 | 150 | 0.5 | 2.96 | 150 | 2.76 | 99.8 |
| 8 | 130 | 0.5 | 1.96 | 130 | 1.76 | 99.5 |
| 9 | 170 | 0.5 | 1.46 | 150 | 1.26 | 99.7 |

As has been described, in accordance with the present invention, high purity lithium N-methylaminobutyrate, which contains only remarkably small amounts of alkali metals other than lithium and does not contain lithium ingredient such as lithium hydroxide which is sparingly soluble in organic solvent, can be produced as a solution in N-methyl-2-pyrrolidone or the like, since lithium hydroxide which is sparingly soluble in N-methyl-2-pyrrolidone and the like and not easily recycled, is not used, but lithium chloride is used, which is easily soluble in aprotic organic solvents such as N-methyl-2-pyrrolidone, which are also suitable for preparation of PAS resins including PPS resins, and N-methyl-2-pyrrolidone is first reacted with hydroxide of an alkali metal other than lithium, water is removed from the reaction product mixture and then the reaction product is reacted with lithium chloride to form lithium N-methylaminobutyrate and finally the formed non-lithium alkali metal chloride such as sodium chloride is removed by solid-liquid separation.

Thus, in the preparation of PAS resins such as PPS resins from lithium N-methylaminobutyrate, a dihaloaromatic compound and hydrogen sulfide, recycled use of the formed lithium chloride, purification of the product polymer, etc. which have been problems in the conventional process, are now solved by using the lithium N-methylaminobutyrate or a solution thereof (especially a N-methyl-2-pyrrolidone solution) obtained by the process of the present invention.

That is to say, the process for preparation of lithium N-methylaminobutyrate of the present invention is a practically excellent process, which exhibits a remarkable effect when it is employed in combination with the preparation of the above mentioned resin. It is also a very useful process for preparation of high purity N-methylaminobutyrate apart from the preparation of PAS resins and, therefore, it is an industrially very valuable process.

What we claim is:

1. A process for preparing lithium N-methylaminobutyrate comprising reacting N-methyl-2-pyrrolidone with a hydroxide of an alkali metal other than lithium in an aprotic organic solvent, reacting the resulting reaction product mixture with lithium chloride after removing water therefrom and removing the alkali metal chloride formed as a by-product.

2. The process for preparing lithium N-methylaminobutyrate claimed in claim 1, wherein the removal of water from the reaction product mixture is effected until the water content thereof becomes 500 wtppm.

3. The process for preparing lithium N-methylaminobutyrate claimed in claim 1, wherein the aprotic solvent used is at least one selected from amide compounds, lactam compounds and urea compounds.

4. The process for preparing lithium N-methylaminobutyrate claimed in claim 3, wherein the aprotic solvent used is a lactam compound.

5. The process for preparing lithium N-methylaminobutyrate claimed in claim 3, wherein the aprotic solvent used is a N-methyl-2-pyrrolidone.

6. The process for preparing lithium N-methylaminobutyrate claimed in claim 1, wherein the alkali metal hydroxide to be reacted with N-methyl-2-pyrrolidone is selected from sodium hydroxide, potassium hydroxide, rubidium hydroxide, cesium hydroxide and a mixture of two or more thereof.

7. The process for preparing lithium N-methylaminobutyrate claimed in claim 6, wherein the alkali metal hydroxide to be reacted with N-methyl-2-pyrrolidone is sodium hydroxide or potassium hydroxide.

8. The process for preparing lithium N-methylaminobutyrate claimed in claim 1, wherein sodium hydroxide is used as the hydroxide of an alkali metal other than lithium, and N-methyl-2-pyrrolidone is used in an amount of 1.05–30 mol per mol of the hydroxide of the alkali metal other than lithium.

9. The process for preparing lithium N-methylaminobutyrate claimed in claim 1, wherein the aprotic organic solvent used is other than N-methyl-2-pyrrolidone and N-methyl-2-pyrrolidone is used in an amount of 1.5–30 mol per mol of alkali metal hydroxide other than lithium hydroxide.

10. The process for preparing lithium N-methylaminobutyrate claimed in claim 1, wherein the hydroxide of an alkali metal other than lithium is reacted with N-methyl-2-pyrrolidone in the form of an aqueous solution and the content of said hydroxide of an alkali metal other than lithium is 5–90 wt %.

11. The process for preparing lithium N-methylaminobutyrate claimed in claim 1, wherein the reaction of N-methyl-2-pyrrolidone and the hydroxide of an alkali metal other than lithium is conducted at a temperature of 100°–200° C.

12. The process for preparing lithium N-methylaminobutyrate claimed in claim 7, wherein from the reaction product mixture containing lithium N-methylaminobutyrate and lithium chloride, which has been obtained by the reaction of lithium chloride and sodium N-methylaminobutyrate, sodium chloride is removed by deposition at 80°–200° C.

* * * * *